(12) United States Patent
Banowski et al.

(10) Patent No.: US 10,688,322 B2
(45) Date of Patent: Jun. 23, 2020

(54) USE OF POLYSACCHARIDES IN ANTIPERSPIRANT COSMETIC AGENTS FOR PROTECTING TEXTILES

(71) Applicant: Henkel AG & Co. KGaA, Duesseldorf (DE)

(72) Inventors: Bernhard Banowski, Duesseldorf (DE); Marcus Claas, Hilden (DE); Imme Breuer, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/077,434

(22) Filed: Mar. 22, 2016

(65) Prior Publication Data

US 2016/0199284 A1    Jul. 14, 2016

Related U.S. Application Data

(63) Continuation of application No. PCT/DE2014/200518, filed on Sep. 26, 2014.

(30) Foreign Application Priority Data

Oct. 15, 2013 (DE) .................. 10 2013 220 767

(51) Int. Cl.
| | | |
|---|---|---|
| *A61Q 15/00* | (2006.01) | |
| *A61K 8/26* | (2006.01) | |
| *A61K 8/73* | (2006.01) | |
| *C11D 3/00* | (2006.01) | |
| *C11D 3/22* | (2006.01) | |

(52) U.S. Cl.
CPC .............. *A61Q 15/00* (2013.01); *A61K 8/26* (2013.01); *A61K 8/731* (2013.01); *C11D 3/0021* (2013.01); *C11D 3/222* (2013.01); *A61K 2800/40* (2013.01)

(58) Field of Classification Search
CPC .......... A61Q 15/00; A61K 8/26; A61K 8/731; A61K 2800/40; C11D 3/0021; C11D 3/222
See application file for complete search history.

(56) References Cited

U.S. PATENT DOCUMENTS

| | | | |
|---|---|---|---|
| 2,571,030 A | 10/1951 | Govett et al. | |
| 3,887,692 A | 6/1975 | Gilman | |
| 3,904,741 A | 9/1975 | Jones et al. | |
| 3,974,270 A | 8/1976 | Kenkare et al. | |
| 4,017,599 A | 4/1977 | Rubino | |
| 4,359,456 A | 11/1982 | Gosling et al. | |
| 4,511,554 A | 4/1985 | Geria et al. | |
| 4,775,528 A | 10/1988 | Callaghan et al. | |
| 5,643,558 A | 7/1997 | Provancal et al. | |
| 5,925,338 A | 7/1999 | Karassik et al. | |
| 6,010,688 A | 1/2000 | Shen | |
| 6,042,816 A | 3/2000 | Shen | |
| 6,074,632 A | 6/2000 | Shen | |
| 6,245,325 B1 | 6/2001 | Shen | |
| 6,436,381 B1 | 8/2002 | Carrillo et al. | |
| 6,649,152 B2 | 11/2003 | Carrillo et al. | |
| 6,663,854 B1 | 12/2003 | Shen et al. | |
| 6,923,952 B2 | 8/2005 | Allen et al. | |
| 7,105,691 B2 | 9/2006 | Holerca et al. | |
| 8,691,250 B2 | 4/2014 | Urban et al. | |
| 10,076,482 B2 * | 9/2018 | Aubrun .................. | A61K 8/342 |
| 2004/0009133 A1 | 1/2004 | Kolodzik et al. | |
| 2010/0196515 A1* | 8/2010 | Kamiya ............... | A61K 8/0229 |
| | | | 424/684 |
| 2014/0090183 A1* | 4/2014 | Urban ...................... | A61K 8/26 |
| | | | 8/137 |
| 2014/0093463 A1 | 4/2014 | Urban et al. | |
| 2014/0093464 A1 | 4/2014 | Urban et al. | |
| 2014/0105841 A1 | 4/2014 | Urban et al. | |

FOREIGN PATENT DOCUMENTS

| | | |
|---|---|---|
| DE | 102006004957 A1 | 8/2007 |
| DE | 102011083872 A1 | 6/2012 |
| EP | 0676192 A2 | 10/1995 |
| GB | 1347950 | 2/1974 |
| GB | 2048229 A | 12/1980 |
| WO | 2013/092185 A2 | 6/2013 |

OTHER PUBLICATIONS

PCT International Search Report (PCT/DE2014/200518) dated Jan. 19, 2015.

* cited by examiner

*Primary Examiner* — Robert S Cabral
(74) *Attorney, Agent, or Firm* — P. Scott Smith

(57) ABSTRACT

The present invention relates to the use of a polysaccharide selected from the group of non-modified polysaccharides, chemically modified polysaccharides and physically modified polysaccharides, in antiperspirant cosmetic agents, the use of these polysaccharides resulting in an excellent reduction and/or prevention of textile discoloration and/or textile stains.

9 Claims, No Drawings

USE OF POLYSACCHARIDES IN ANTIPERSPIRANT COSMETIC AGENTS FOR PROTECTING TEXTILES

FIELD OF THE INVENTION

The present invention generally relates to a use of at least one polysaccharide in antiperspirant cosmetic agents for reducing and/or preventing textile soiling and/or textile discolorations. The present invention further relates to a method for reducing and/or preventing textile soiling and/or textile discolorations using a polysaccharide in an antiperspirant cosmetic agent.

BACKGROUND OF THE INVENTION

Washing, cleaning, and caring for one's body is a basic human need, and modern industry is continually attempting to satisfy these needs of humans in a variety of ways. The lasting elimination, or at least reduction, of body odor and underarm perspiration is particularly important for daily hygiene. Numerous special deodorizing or antiperspirant body care agents are known in the related art, which were developed for use in body regions that have a high density of sweat glands, in particular in the axilla region. These are formulated in a wide variety of forms of administration, for example as powders, in stick form, as aerosol sprays, pump sprays, liquid and gel-like roll-on applications, creams, gels, and as saturated flexible substrates (deodorant wipes).

In addition to at least one oil or a fat substance and an odorous substance component or a perfume, cosmetic antiperspirants of the related art include at least one antiperspirant salt.

When used regularly, antiperspirants can result in clearly visible colored textile soils. These are often white and/or greasy and/or yellow stains, which cannot be removed either with intensive washing. The staining is based on a complex interaction between formulation components of the antiperspirant, sweat, and the detergent used. It is likely that initially insoluble aluminum compounds form on and within the fiber. Yellowing generally develops with some time delay and is caused at least partially by the oxidation of unsaturated fatty acids or other organic compounds present as insoluble aluminum salts or in fixed form on the stain. The intensity of the staining on the textile is in particular dependent on the composition of the antiperspirant product, the type of perfume oil in the antiperspirant, the detergent, and the individual amount and composition of the stain.

Moreover, certain components of the formulation, such as hydrophobic sequestering agents, can result in dark, greasy/oil stains on the textile. The hydrophobic sequestering agents in the form of cosmetic oils or polyols are used to prevent white residue of the antiperspirant on dark textiles, which may develop, for example, as a result of the antiperspirants being transferred from the skin onto a textile during dressing. However, depending on the chemical composition, these sequestering agents can be removed only partially or not at all by a standard washing process, whereby the aforementioned stains are created, which can also alter the feel of the textiles in the soiled region.

In addition, the interaction between detergents and active antiperspirant ingredients can create further insoluble compounds, which can attach to the textile. These insoluble compounds form white, hard residue, which generally does not appear on the textile until after several soiling and washing cycles. This white residue is not soluble in water and also cannot be removed by standard washing methods. It is particularly apparent on light-colored or dark dyed textiles.

Various ingredients are added in the related art to protect textiles against such permanent soiling. One frequently used additive is surfactants, as described in document WO 2010/097205 A2, for example. The selection of the oil components may also reduce the textile soiling, or it may increase it, as described in documents U.S. Pat. No. 5,925,338 A, 4,511,554 A or 3,974,270 A.

As a result, there is a continued need for ingredients in antiperspirants that are able to effectively reduce and/or prevent the above-described soils, even with a long-term use of antiperspirants.

It was the object of the present invention to provide an ingredient in antiperspirant cosmetic agents that prevents, or at least lessens, the drawbacks from the prior art and is able to reduce and/or prevent textile discolorations and/or textile stains, without adversely affecting the action of the antiperspirant cosmetic agent or the shelf life of the same.

Surprisingly, it was now found that the use of special polysaccharides in antiperspirant cosmetic agents reduces and/or prevents textile soiling and/or textile stains, however without adversely affecting the action of the antiperspirant cosmetic agent and the shelf life of the same.

Furthermore, other desirable features and characteristics of the present invention will become apparent from the subsequent detailed description of the invention and the appended claims, taken in conjunction with this background of the invention.

BRIEF SUMMARY OF THE INVENTION

Use of a polysaccharide, selected from the group consisting of chemically modified polysaccharides, physically modified polysaccharides, and unmodified polysaccharides in antiperspirant cosmetic agents for reducing and/or preventing textile discolorations and/or textile stains.

Use of an antiperspirant cosmetic agent, comprising: at least one substance selected from the group consisting of cosmetic oils that are liquid at 20° C. and 1,013 hPa, odorous substances and waxes; at least one antiperspirant aluminum salt in a total amount of 1 to 80 wt. %, based on the total weight of the antiperspirant cosmetic agent; and at least one polysaccharide selected from the group consisting of the chemically modified polysaccharides, physically modified polysaccharides, and unmodified polysaccharides for reducing and/or preventing textile discolorations and/or textile stains.

A method for preventing and/or reducing textile discolorations and/or textile stains, wherein the method comprises the following method steps: producing an antiperspirant cosmetic agent by mixing an antiperspirant aluminum salt with at least one polysaccharide and optionally further ingredients and optionally propellants; applying the antiperspirant cosmetic agent to the skin, in particular to the skin of the axilla; wearing a piece of textile clothing over the treated skin; and washing the piece of textile clothing, in particular washing the piece of textile clothing multiple times, wherein after washing, in particular after multiple instances of washing, no or decreased textile discolorations and/or textile stains occur.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention relates to a use of a polysaccharide, selected from the group consisting of chemically modified polysaccharides, physically modified polysaccharides, and unmodified polysaccharides in antiperspirant cosmetic agents for reducing and/or avoiding textile discolorations and/or textile stains.

Without being limited to this theory, the use of polysaccharides in antiperspirant cosmetic agents prevents an interaction between the residue of the antiperspirant aluminum salt adhering to the textile after application of the antiperspirant cosmetic agent and the detergents used during washing. In this way, the addition of polysaccharides to antiperspirant cosmetic agents prevents or lessens the development of hardly soluble aluminum compounds during the washing process, and thereby significantly reduces the formation of textile discolorations and/or textile stains. Moreover, the addition of polysaccharides to antiperspirant cosmetic agents does not adversely influence the antiperspirant action of these agents or decrease the shelf life of these agents.

The term "physically modified polysaccharides" within the scope of the present invention shall be understood to mean polysaccharides that have been modified by a physical influence, in particular by heat and/or light.

Moreover, the term "antiperspirant cosmetic agent" within the scope of the present invention shall be understood to mean a cosmetic agent that is able to decrease or reduce the perspiration of the body's sweat glands.

In addition, the term 'textile discoloration" or the term "textile stain" within the scope of the present invention shall be understood to mean a soiling of the textile by antiperspirant cosmetic agents, wherein the soiling of the textile can be white and/or greasy and/or yellow.

According to a preferred embodiment of the present invention, the chemically modified polysaccharide is selected from the group consisting of (i) chemically modified celluloses, in particular $C_{1-10}$ alkyl cellulose, hydroxy $C_{2-10}$ alkyl methyl cellulose, hydroxy $C_{2-10}$ alkyl ethyl cellulose, hydroxy $C_{1-10}$ alkyl cellulose, carboxy $C_{1-10}$ alkyl cellulose, and $C_{6-30}$ alkyl hydroxyethyl cellulose;

(ii) chemically modified starches, in particular aluminum starch octenylsuccinate, sodium starch octenylsuccinate, calcium starch octenylsuccinate, dehydrated xanthan gum; and (iii) the mixtures thereof.

It is furthermore preferred within the scope of the present invention if the chemically modified polysaccharide is selected from the group consisting of $C_{1-10}$ alkyl celluloses, hydroxy $C_{2-10}$ alkyl methyl celluloses, hydroxy $C_{2-10}$ alkyl ethyl celluloses, hydroxy $C_{1-10}$ alkyl celluloses, carboxy $C_{1-10}$ alkyl celluloses, and $C_{6-30}$ alkyl hydroxyethyl celluloses.

$C_{6-30}$ alkyl hydroxyethyl celluloses shall be understood to mean such cellulose compounds in which hydrophobic $C_{6-30}$ alkyl groups are bound to the cellulose skeleton by way of ethylene oxide units. By introducing $C_{6-30}$ alkyl groups on ethylene oxide units of the basic structure, these celluloses are of a hydrophobic nature and are also referred to as hydrophobically modified hydroxyethyl celluloses.

Particularly good results with respect to the prevention and/or decrease of textile discolorations and/or textile stains are achieved within the scope of the present invention if the chemically modified polysaccharide is selected from the group consisting of methylcellulose, hydroxyethyl cellulose, hydroxyethyl methyl cellulose, hydroxypropyl cellulose, hydroxypropyl methyl cellulose, hydroxypropyl ethyl cellulose, carboxymethyl cellulose, and cetyl hydroxyethylcellulose. Staining on textiles caused by the formation of insoluble deposits as a result of the interaction between the antiperspirant aluminum salt adhering to the textile and the detergent is avoided or decreased in particular when using the aforementioned polysaccharides in antiperspirant cosmetic agents. The use of the aforementioned polysaccharides therefore results in significantly decreased staining on textiles during the washing process. Moreover, the abovementioned polysaccharides do not adversely affect the antiperspirant action of the aluminum salt.

Within the scope of the present invention, it may also be provided that the unmodified polysaccharide is selected from the group consisting of (i) gums, in particular xanthan gums, alginates, gum arabic, karaya gum, carrageenans, and carob seed powder;

(ii) starches, in particular of corn, potatoes and wheat;

(iii) celluloses; and (iv) the mixtures thereof.

Within the scope of the present invention, it may furthermore be provided that the physically modified polysaccharide is selected from the group consisting of microcrystalline celluloses, pregelatinized starches, and the mixtures thereof.

The present invention further relates to the use of antiperspirant cosmetic agents, including a) at least one substance selected from the group consisting of cosmetic oils that are liquid at 20° C. and 1,013 hPa, odorous substances and waxes;

b) at least one antiperspirant aluminum salt in a total amount of 1 to 80 wt. %, based on the total weight of the antiperspirant cosmetic agent; and c) at least one polysaccharide selected from the group consisting of the unmodified polysaccharides, chemically modified polysaccharides, and physically modified polysaccharides;

for reducing and/or preventing textile discolorations and/or textile stains. It is particularly preferred according to the invention to reduce and/or prevent textile discolorations and/or textile stains by deodorant and/or antiperspirant products.

The use of special polysaccharides in aluminum salt-containing antiperspirant cosmetic agents allows soiling of textiles during the washing process as a result of the formation of insoluble aluminum salt residues with the ingredients of the detergent to be prevented or decreased. Moreover, use of the special polysaccharides does not adversely affect the antiperspirant action of the cosmetic agent.

The term "cosmetic oil" within the meaning of the present invention shall be understood to mean an oil that is suitable for cosmetic use and not miscible with water. The cosmetic oil used according to the invention furthermore involves neither odorous substances nor essential oils.

Finally, the term "odorous substances" within the meaning of the present invention shall be understood to mean substances having a molar mass of 74 to 300 g/mol, which include at least one osmophoric group in the molecule and have an odor and/or a flavor, which is to say they are capable of stimulating the receptors of the hair cells of the olfactory system. Osmophoric groups are groups that are covalently bonded to the molecular skeleton in the form of hydroxy groups, formyl groups, oxo groups, alkoxy carbonyl groups, nitrile groups, nitro groups, azide groups and the like. In this connection, the term "odorous substances" within the meaning of the present invention also covers perfume oils, perfumes, or perfume oil components that are liquid at 20° C. and 1,013 hPa.

Moreover, the term "waxes" within the scope of the present invention shall be understood to mean substances that are kneadable or solid to brittle-hard at 20° C., have a coarse to microcrystalline structure, and are translucent to colors to opaque, but not vitreous. These substances furthermore melt above 25° C. without decomposing, are easily liquid (low viscosity) just above the melting point, have a highly temperature-dependent consistency and solubility, and can be polished under light pressure.

The term "volatile cosmetic oil" according to the invention refers to cosmetic oils that, at 20° C. and an ambient pressure of 1,013 hPa, have a vapor pressure of 2.66 Pa to 40,000 Pa (0.02 to 300 mm Hg), especially of 10 to 12,000 Pa (0.1 to 90 mm Hg), more preferably of 13 to 3,000 Pa (0.1 to 23 mm Hg), and in particular of 15 to 500 Pa (0.1 to 4 mm Hg).

Moreover, the term "non-volatile cosmetic oils" within the meaning of the present invention shall be understood to mean cosmetic oils that, at 20° C. and an ambient pressure of 1,013 hPa, have a vapor pressure of less than 2.66 Pa (0.02 mm Hg).

Furthermore, the term "fatty acid", as it is used within the scope of the present invention, shall be understood to mean aliphatic carboxylic acids that include unbranched or branched carbon groups having 4 to 40 carbon atoms. The fatty acids used within the scope of the present invention can be both naturally occurring and synthetically produced fatty acids. The fatty acids can moreover be monounsaturated or polyunsaturated.

Finally, the term "fatty alcohol" within the scope of the present invention shall be understood to mean aliphatic, monohydric, primary alcohols that include unbranched or branched hydrocarbon groups having 4 to 40 carbon atoms. The fatty alcohols used within the scope of the invention can also be monounsaturated or polyunsaturated.

Unless indicated otherwise, in the present invention the wt. % information refers to the total weight of the antiperspirant cosmetic agents used according to the invention, without optionally present propellants.

It may be provided within the scope of the present invention that the cosmetic oil that is liquid at 20° C. and 1,013 hPa is selected from the group consisting of (i) volatile cyclic silicone oils, in particular cyclotrisiloxane, cyclotetrasiloxane, cyclopentasiloxane, and cyclohexasiloxane, and linear silicone oils having 2 to 10 siloxane units, in particular hexamethyldisiloxane, octamethyltrisiloxane, decamethyltetrasiloxane;

(ii) volatile non-silicone oils, in particular liquid paraffin oils and isoparaffin oils, such as isodecane, isoundecane, isododecane, isotridecane, isotetradecane, isopentadecane, isohexadecane, and isoeicosane;

(iii) non-volatile silicone oils, in particular higher molecular weight polyalkylsiloxanes;

(iv) non-volatile non-silicone oils, in particular the esters of linear or branched saturated or unsaturated $C_{2-30}$ fatty alcohols having linear or branched saturated or unsaturated $C_{2-30}$ fatty acids, which may be hydroxylated, the $C_8$ to $C_{22}$ fatty alcohol esters of monovalent or polyvalent $C_2$ to $C_7$ hydroxycarboxylic acids, the triethyl citrates, the branched saturated or unsaturated $C_{6-30}$ fatty alcohols, the mono-, di- and triglycerides of linear or branched, saturated or unsaturated, optionally hydroxylated $C_{8-30}$ fatty acids, the dicarboxylic acid esters of linear or branched $C_2$ to $C_{10}$ alkanols, the addition products of ethylene oxide and/or propylene oxide to monohydric or polyhydric $C_{3-22}$ alkanols, which may optionally be esterified, the symmetrical, asymmetrical or cyclic esters of carbonic acid with fatty alcohols, the esters of dimers of unsaturated $C_{12-22}$ fatty acids with monohydric, linear, branched and cyclic $C_{2-18}$ alkanols or $C_{2-6}$ alkanols, the benzoic acid esters of linear or branched $C_{8-22}$ alkanols, such as benzoic acid-$C_{12-15}$-alkyl esters and benzoic acid isostearyl esters and benzoic acid octyldodecyl esters, the synthetic hydrocarbons, such as polyisobutene and polydecene, the alicyclic hydrocarbons; and (v) the mixtures thereof.

The use of volatile silicone oils and volatile non-silicone oils within the scope of the use according to the invention of the antiperspirant cosmetic agents results in a dryer skin sensation and a more rapid release of the antiperspirant aluminum salt.

The cyclic volatile silicone oils usable within the scope of the invention have a vapor pressure of 13 to 15 Pa (0.1 mm Hg) at 20° C. and an ambient pressure of 1,013 hPa. Moreover, it is also possible according to the invention to use a low molecular weight phenyl trimethicone having a vapor pressure of approximately 2,000 Pa (15 mm Hg) at 20° C. and an ambient pressure of 1,013 hPa as the linear volatile silicone oil. Due to the high persistence of cyclodimethicones in the environment, however, it may be preferred according to the invention if the antiperspirant cosmetic agents according to the invention include 0 to less than 1 wt. %, especially 0 to less than 0.1 wt. %, cyclic volatile silicone oils.

According to the invention, preferably volatile non-silicone oils in the form of $C_{10-13}$ isoparaffin mixtures having a vapor pressure of 10 to 400 Pa (0.08 to 3 mm Hg), especially of 13 to 100 Pa (0.1 to 0.8 mm Hg), at 20° C. and an ambient pressure of 1,013 hPa are used. It is preferred within the scope of the present invention if the volatile $C_8$ to $C_{16}$ isoparaffin is present in a total amount of 1 to 90 wt. %, especially of 3 to 45 wt. %, preferably of 5 to 40 wt. %, and in particular of 8 to 20 wt. %, based on the total weight of the antiperspirant cosmetic agent. Of course it is likewise possible to formulate antiperspirant cosmetic agents that are used according to the invention with a low content of volatile oils, which is to say with 0.1 to 15 wt. %, based on the total weight of the antiperspirant cosmetic agent, of volatile oils, or even without volatile oils.

So as to mask insoluble components, such as talcum or antiperspirant aluminum salts dried on the skin, it may be preferred if the antiperspirant cosmetic agents used according to the invention include a non-volatile silicone oil and/or a non-volatile non-silicone oil.

In this connection, antiperspirant cosmetic agents that are preferably used according to the invention include at least one ester of the linear or branched saturated or unsaturated fatty alcohols including 2 to 30 carbon atoms with linear or branched saturated or unsaturated fatty acids including 2 to 30 carbon atoms, which may be hydroxylated, in a total amount of 1 to 30 wt. %, especially of 5 to 26 wt. %, preferably of 9 to 24 wt. %, and in particular of 12 to 17 wt. %, based on the total weight of the antiperspirant cosmetic agent. However, it may also be provided that the antiperspirant cosmetic agents that are used according to the invention include at least one ester of the linear or branched saturated or unsaturated fatty alcohols including 2 to 30 carbon atoms with linear or branched saturated or unsaturated fatty acids including 2 to 30 carbon atoms, which may be hydroxylated, in a total amount of 1 to 90 wt. %, especially of 5 to 60 wt. %, preferably of 9 to 35 wt. %, and in particular of 12 to 17 wt. %, based on the total weight of the antiperspirant cosmetic agent.

Within the scope of the present invention, linear polyalkylsiloxanes having a kinematic viscosity at 25° C. of 5 to 2,000 cSt, in particular linear polydimethylsiloxanes having a kinematic viscosity at 25° C. of 5 to 2,000 cSt, especially of 10 to 350 cSt, and in particular of 50 to 100 cSt, can be used as non-volatile silicone oils. The above-mentioned non-volatile silicone oils are available under the trade name Dow Corning® 200 and Xiameter PMX from Dow Corning and Xiameter, respectively. Further preferred non-volatile silicone oils are phenyl trimethicones having a kinematic viscosity at 25° C. of 10 to 100 cSt, especially of 15 to 30 cSt, and cetyl dimethicones.

Further preferred according to the invention is the use of mixtures of the above-mentioned cosmetic oils, in particular of non-volatile and volatile cosmetic oils, since in this way parameters such as skin sensation and stability of the antiperspirant cosmetic agent used according to the invention can be set, and the use of the agent can thus be better adapted to the needs of the consumers.

It is preferred within the scope of the present invention if the cosmetic oil that is liquid at 20° C. and 1,013 hPa is present in a total amount of 1 to 95 wt. %, especially of 10 to 85 wt. %, preferably of 20 to 70 wt. %, more preferably of 35 to 70 wt. %, and in particular of 50 to 60 wt. %, based on the total weight of the antiperspirant cosmetic agent.

However, it may also be preferred if the cosmetic oil that is liquid at 20° C. and 1,013 hPa is present in a total amount of 0.2 to 70 wt. %, especially of 2 to 60 wt. %, preferably of 3 to 50 wt. %, more preferably of 5 to 35 wt. %, and in particular of 8 to 20 wt. %, based on the total weight of the antiperspirant cosmetic agent. In this connection, it may also be provided that the antiperspirant agents used according to the invention include less than 0.2 wt. %, especially less than 0.1 wt. %, in particular 0 wt. % of the cosmetic oil that is liquid at 20° C. and 1,013 hPa. The use of only extremely small amounts of the cosmetic oil that is liquid at 20° C. and 1,013 hPa is preferred in particular in antiperspirant cosmetic agents used according to the invention which are present in aqueous, aqueous-alcoholic or aqueous-glycolic form.

According to a preferred embodiment of the present invention, the odorous substance is selected from the group consisting of
(i) esters, in particular benzyl acetate, phenoxyethyl isobutyrate, p-tert.-butylcyclohexyl acetate, linalyl acetate, dimethyl benzyl carbinyl acetate (DMBCA), phenylethyl acetate, benzyl acetate, ethyl methylphenylglycinate, allyl cyclohexyl propionate, styrallyl propionate, benzyl salicylate, cyclohexyl salicylate, floramate, melusate, and jasmecyclate;
(ii) ethers, in particular benzyl ethyl esters and Ambroxan;
(iii) aldehydes, in particular linear alkanals having 8 to 18 carbon atoms, citral, citronellal, citronellyl oxy acetaldehyde, cyclamen aldehyde, lilial and bourgeonal;
(iv) ketones, in particular jonone, alpha-isomethyl ionone and methyl cedryl ketone;
(v) alcohols, in particular anethol, citronellol, eugenol, geraniol, linalool, phenylethyl alcohol and terpineol;
(vi) hydrocarbons, in particular terpenes such as limonene and pinene; and
(vii) the mixtures thereof.

Preferably, however, mixtures of different odorous substances are used that together produce an appealing odorous note.

Antiperspirant cosmetic agents used according to the invention that have a particularly appealing odor are obtained when the odorous substance is present in a total amount of 0.00001 to 10 wt. %, especially 0.001 to 9 wt. %, preferably 0.01 to 8 wt. %, more preferably 0.5 to 7 wt. %, and in particular 1 to 6 wt. %, based on the total weight of the antiperspirant cosmetic agent. In this connection, however, it may also be provided that the odorous substance is present in a total amount of 0.00001 to 5 wt. %, especially 0.001 to 4 wt. %, preferably 0.01 to 3 wt. %, more preferably 0.1 to 2 wt. %, and in particular 0.2 to 1.5 wt. %, based on the total weight of the propellant-containing antiperspirant cosmetic agent.

According to a further preferred embodiment of the present invention, the wax is selected from the group consisting of
(i) fatty acid glycerol mono-, di-, and triesters;
(ii) Butyrospermum Parkii (shea butter);
(iii) esters of saturated, monohydric $C_{8-18}$ alcohols with saturated $C_{12-16}$ monocarboxylic acids;
(iv) linear primary $C_{12}$ to $C_{24}$ alkanols;
(v) esters of a saturated, monohydric $C_{16}$ to $C_{60}$ alkanol and a saturated $C_8$ to $C_{36}$ monocarboxylic acid, in particular cetyl behenate, stearyl behenate, and $C_{20}$ to $C_{40}$ alkyl stearate;
(vi) glycerol triesters of saturated linear $C_{12}$ to $C_{30}$ carboxylic acids, which may be hydroxylated, in particular hydrogenated palm oil, hydrogenated coconut oil, hydrogenated castor oil, glyceryl tribehenate, and glyceryltri12-hydroxy stearate;
(vii) natural plant-based waxes, in particular candelilla wax, carnauba wax, Japan wax, sugarcane wax, ouricoury wax, cork wax, sunflower wax, fruit waxes;
(viii) animal waxes, in particular beeswax, shellac wax, and cetaceum;
(ix) synthetic waxes, in particular montan ester waxes, hydrogenated jojoba waxes and sasol waxes, polyalkylene waxes and polyethylene glycol waxes, $C_{20}$ to $C_{40}$ dialkyl esters of dimer acids, $C_{30\text{-}50}$ alkyl beeswax, and alkyl and alkyl aryl esters of dimeric fatty acids, paraffin waxes; and
(x) the mixtures thereof.

Commercial products bearing the INCI name Cocoglycerides, in particular the commercial products Novata® (from BASF), particularly preferably Novata® AB, a mixture of $C_{12-18}$ mono-, di-, and triglycerides that melts in the range from 30 to 32° C., and the products of the Softisan series (Sasol Germany GmbH) bearing the INCI name Hydrogenated Cocoglycerides, in particular Softisan 100, 133, 134, 138, 142, are particularly preferred. Further preferred esters of saturated, monohydric $C_{12-18}$ alcohols with saturated $C_{12-18}$ monocarboxylic acids are stearyl laurate, cetearyl stearate (such as Crodamol® CSS), cetyl palmitate (such as Cutina® CP), and myristyl myristate (such as Cetiol® MM). Furthermore a $C_{20}$ to $C_{40}$ alkyl stearate is preferably used as the wax component. This ester is known under the name Kester Wax® K82H or Kester Wax® K80H and is sold by Koster Keunen Inc.

It is preferred within the scope of the present invention if the wax is present in a total amount of 0.01 to 20 wt. %, especially 3 to 20 wt. %, preferably 5 to 18 wt. %, and in particular 6 to 15 wt. %, based on the total weight of the antiperspirant cosmetic agent.

A particularly good antiperspirant action with the use according to the invention is achieved when the antiperspirant aluminum salt is present in a total amount of 2 to 40 wt. %, especially 3 to 35 wt. %, preferably 4 to 32 wt. %, more preferably 5 to 28 wt. %, still more preferably 8 to 25 wt. %, and in particular 12 to 22 wt. %, based on the total weight of the antiperspirant cosmetic agent. However, it may also be provided that the antiperspirant aluminum salt is present in a total amount of 0.1 to 20 wt. %, especially 0.5 to 15 wt. %, preferably 1 to 12 wt. %, more preferably 1.5 to 10 wt. %, and in particular 2 to 8 wt. %, based on the total weight of the propellant-containing antiperspirant composition.

Within the scope of the present invention, the antiperspirant aluminum salt may be selected from the group consisting of (i) water-soluble astringent inorganic salts of aluminum, in particular aluminum chlorohydrate, aluminum sesquichlorohydrate, aluminum dichlorohydrate, aluminum hydroxide, potassium aluminum sulfate, aluminum bromohydrate, aluminum chloride, aluminum sulfate;

(ii) water-soluble astringent organic salts of aluminum, in particular aluminum chlorohydrex propylene glycol, aluminum chlorohydrex polyethylene glycol, aluminum propylene glycol complexes, aluminum sesquichlorohydrex propylene glycol, aluminum sesquichlorohydrex polyethylene glycol, aluminum propylene glycol dichlorohydrex, aluminum polyethylene glycol dichlorohydrex, aluminum undecylenoyl collagen amino acid, sodium aluminum lactate, sodium aluminum chlorohydroxy lactate, aluminum lipoamino acids, aluminum lactate, aluminum chlorohydroxy allantoinate, sodium aluminum chlorohydroxy lactate;

(iii) water-soluble astringent inorganic aluminum-zirconium salts, in particular aluminum-zirconium trichlorohydrate, aluminum-zirconium tetrachlorohydrate, aluminum-zirconium pentachlorohydrate, aluminum-zirconium octachlorohydrate;

(iv) water-soluble astringent organic aluminum-zirconium salts, in particular aluminum-zirconium propylene glycol complexes, aluminum-zirconium trichlorohydrex glycine, aluminum-zirconium tetrachlorohydrex glycine, aluminum-zirconium pentachlorohydrex glycine, aluminum-zirconium octachlorohydrex glycine; and (v) the mixtures thereof.

According to the invention, the term "antiperspirant aluminum salts" shall be understood not to include any aluminosilicates and zeolites. Moreover, according to the invention "water-soluble aluminum salts" shall be understood to mean those salts which have a solubility of at least 3 wt. % at 20° C., which is to say at least 3 g of the antiperspirant aluminum salt dissolves in 97 g of water at 20° C.

Particularly preferred inorganic aluminum salts are selected from aluminum chlorohydrate, in particular aluminum chlorohydrate of the general formula $[Al_2(OH)_5Cl.1\text{-}6H_2O]_n$, preferably $[Al_2(OH)_5Cl.2\text{-}3H_2O]_n$, which may be present in non-activated (polymerized) or in activated (depolymerized) form, and aluminum chlorohydrate of the general formula $[Al_2(OH)_4Cl_2.1\text{-}6H_2O]_n$, preferably $[Al_2(OH)_4Cl_2.2\text{-}3H_2O]_n$, which may be present in non-activated (polymerized) or in activated (depolymerized) form. The production of such antiperspirant aluminum salts is disclosed in documents U.S. Pat. Nos. 3,887,692 A, 3,904,741 A, 4,359,456 A, GB 2 048 229 A, and GB 1 347 950 A, for example.

Particularly preferred antiperspirant aluminum salts according to the invention are selected from what are known as "activated" aluminum salts, which are also referred to as enhanced-activity active antiperspirant ingredients. Such active ingredients are known from the prior art and are also commercially available. Production of the same is disclosed in documents GB 2 048 229 A, U.S. Pat. Nos. 4,775,528 A, and 6,010,688 A. Activated aluminum salts are generally produced by heat treating a dilute solution of the corresponding salt (such as a solution containing 10 wt. % salt), so as to increase the HPLC peak 4 to peak 3 area ratio of the same. The activated salt can subsequently be dried to obtain a powder, in particular spray-dried. In addition to spray drying, drum drying also suited, for example. Activated aluminum salts typically have an HPLC peak 4 to peak 3 area ratio of at least 0.4, especially at least 0.7, and in particular at least 0.9, wherein at least 70% of the aluminum can be assigned to these HPLC peaks.

In this connection, "activated" aluminum-zirconium salts are likewise known, which have a high HPLC peak 5 aluminum content, in particular a peak 5 area of at least 33%, especially at least 45%, based on the total surface area under peaks 2-5, as measured with HPLC, of a 10% by weight aqueous solution of the active ingredient under conditions in which the aluminum species are dissolved in at least four successive peaks (referred to as peaks 2-5). Preferred aluminum-zirconium salts having a high HPLC peak 5 aluminum content (also referred to as "$E^5AZCH$") are disclosed in documents U.S. Pat. Nos. 6,436,381 A and 6,649,152 A, for example. Furthermore, the above-mentioned activated aluminum-zirconium salts can additionally be stabilized with a water-soluble strontium salt and/or a water-soluble calcium salt, as they are disclosed in document U.S. Pat. No. 6,923,952 A, for example.

It is likewise possible according to the invention to use antiperspirant aluminum salts as non-aqueous solutions or solubilizates of an activated antiperspirant aluminum or aluminum-zirconium salt, for example in accordance with document U.S. Pat. No. 6,010,688 A. As a result of the addition of an effective amount of a polyhydric alcohol comprising 3 to 6 carbon atoms and 3 to 6 hydroxyl groups, preferably propylene glycol, sorbitol and pentaerythritol, such aluminum or aluminum-zirconium salts are stabilized against the loss of the activation of the salt Particularly preferred are also complexes of activated antiperspirant aluminum or aluminum-zirconium salts, comprising a polyhydric alcohol, which include 20 to 50 wt. %, especially 20 to 42 wt. %, activated antiperspirant aluminum or aluminum-zirconium salt and 2 to 16 wt. % molecularly bound water, wherein the remainder to make up 100 wt. % is at least one polyhydric alcohol comprising 3 to 6 carbon atoms and 3 to 6 hydroxyl groups. Propylene glycol, propylene glycol/sorbitol mixtures, and propylene glycol/pentaerythritol mixtures are preferred such alcohols. Such preferred complexes according to the invention of an activated antiperspirant aluminum or aluminum-zirconium salt including a polyhydric alcohol are disclosed in documents U.S. Pat. Nos. 5,643,558 A and 6,245,325 A for example.

It is likewise possible within the scope of the present invention to use alkaline calcium-aluminum salts, as they are disclosed in document U.S. Pat. No. 2,571,030 A, for example, as antiperspirant aluminum salts. These salts can be obtained by reacting calcium carbonate with aluminum chlorohydroxide or aluminum chloride and aluminum powder, or by adding calcium chloride dihydrate to aluminum chlorohydroxide. However, it is likewise possible to use aluminum-zirconium complexes that are buffered with salts of amino acids, in particular with alkali and alkaline earth glycinates, as they are disclosed in document U.S. Pat. No. 4,017,599 A, for example.

The aluminum or aluminum-zirconium salts listed in the documents U.S. Pat. No. 6,245,325 A, 6,042,816 A, 6,245,325 A, 6,042,816 A, 6,245,325 A, 6,042,816 A, 6,245,325 A, 6,042,816 A or 7,105,691 A can also be used as preferred antiperspirant activated aluminum and aluminum-zirconium salts according to the invention, which are preferably stabilized by amino acids, in particular glycine, hydroxyalkanoic acids, in particular glycolic acid and lactic acid, or betaines.

Further preferred activated aluminum salts are those of the general formula $Al_2(OH)_{6-a}Xa$, where X is Cl, Br, I or $NO_3$, and "a" is a number from 0.3 to 5, especially from 0.8 to 2.5, and in particular from 1 to 2, so that the molar ratio of Al:X is 0.9:1 to 2.1:1. Such activated antiperspirant aluminum salts are disclosed in document U.S. Pat. No. 6,074,632 A, for example. Aluminum chlorohydrate (which is to say X is Cl in the aforementioned formula) is particularly preferred, and specifically 5/6 alkaline aluminum chlorohydrate, where "a" is 1, so that the molar ratio of aluminum to chlorine is 1.9:1 to 2.1:1.

Preferred activated aluminum-zirconium salts are those of the general formula $ZrO(OH)_{2-pb}Y_b$, where Y is Cl, Br, I, $NO_3$ or $SO_4$, b is a rational number from 0.8 to 2, and p is the valence of Y, so that the molar ratio of Al—Zr is 2 to 10, and the ratio of metal:(X+Y) is from 0.73 to 2.1, especially from 0.9 to 1.5. Such activated antiperspirant aluminum-zirconium salts are disclosed in the aforementioned document U.S. Pat. No. 6,074,632 A, for example. A particularly preferred salt is aluminum-zirconium chlorohydrate (which is to say X and Y are Cl), which has an Al:Zr ratio of 2 to 10 and a metal:Cl molar ratio of 0.9 to 2.1. Preferred active antiperspirant ingredients are disclosed in documents U.S. Pat. No. 6,663,854 A and US 2004/0009133 A1.

Antiperspirant aluminum salts that are particularly preferred according to the invention have a metal-to-chloride molar ratio of 1.9 to 2.1. The metal-to-chloride ratio of likewise particularly preferred aluminum sesquichlorohydrates within the scope of the invention is 1.5:1 to 1.8:1. Preferred aluminum-zirconium tetrachlorohydrates have a molar ratio of Al:Zr of 2 to 6 and of metal:chloride of 0.9 to 1.3, in particular salts having a metal-to-chloride molar ratio of 0.9 to 1.1, preferably of 0.9 to 1.0, being preferred.

Within the scope of the present invention, a particularly good reduction in textile discolorations and/or textile stains when using the antiperspirant cosmetic agent is achieved when the polysaccharide is present in a total amount of 0.05 to 8 wt. %, especially 0.1 to 7 wt. %, preferably 0.3 to 5 wt. %, more preferably 0.5 to 3 wt. %, still more preferably 0.8 to 2.5 wt. %, in particular 1 to 2 wt. %, based on the total weight of the antiperspirant cosmetic agent. However, it is also possible within the scope of the present invention for the polysaccharide to be present in a total amount of 0.05 to 20 wt. %, especially 0.3 to 18 wt. %, preferably 0.5 to 15 wt. %, more preferably 0.7 to 10 wt. %, still more preferably 1.0 to 9 wt. %, and in particular 1.5 to 6 wt. %, based on the total weight of the antiperspirant cosmetic agent. However, it may also be provided that the polysaccharide is present in a total amount of 0.05 to 20 wt. %, especially 0.3 to 18 wt. %, preferably 0.5 to 15 wt. %, more preferably 0.7 to 10 wt. %, still more preferably 1.0 to 9 wt. %, and in particular 1.5 to 6 wt. %, based on the total weight of the propellant-containing antiperspirant cosmetic agent. Without being limited to this theory, the use of the above-mentioned amounts of the polysaccharide results in a particularly good reduction of textile stains and/or textile discolorations with the use according to the invention of a polysaccharide-containing antiperspirant composition since the aforementioned amounts of polysaccharides effectively prevent or decrease the formation of insoluble residues on textiles due to the reaction between the aluminum salt and components of the detergent. Moreover, the use of the aforementioned amounts of polysaccharides does not adversely influence the antiperspirant action of the cosmetic agent.

What was said with respect to the use according to the invention of polysaccharides in antiperspirant cosmetic agents applies, mutatis mutandis, to particularly preferred polysaccharides that, when used, result in a further decrease of textile stains and/or textile discolorations.

Avoidance of textile discolorations and/or textile stains with the use according to the invention of the antiperspirant cosmetic agents can be further improved if the weight ratio of the antiperspirant aluminum salt to the polysaccharide is from 40:1 to 19:1, especially from 30:1 to 16:1, preferably from 20:1 to 15:1, more preferably from 10:1 to 13:1, still more preferably from 9:1 to 12:1, and in particular from 8:1 to 1:1. The above-mentioned weight ratio refers to the total amount of all antiperspirant aluminum salts and all polysaccharides in the antiperspirant cosmetic agent.

Within the scope of a particularly preferred embodiment, the weight ratio of the antiperspirant aluminum salt to the polysaccharide is 7:1. In addition, the use of a weight ratio of the antiperspirant aluminum salt to the polysaccharide of 10:1 also results in a significant decrease of staining on textiles. Moreover, the use of the aforementioned weight ratios does not adversely influence the antiperspirant action nor the shelf life of the antiperspirant cosmetic agent due to the use of polysaccharides.

According to a further embodiment of the present invention, the antiperspirant cosmetic agent used according to the invention comprises no zirconium-containing compounds.

The antiperspirant cosmetic agent used according to the invention preferably includes free water in a total amount of less than 10 wt. %, especially of less than 8 wt. %, preferably of less than 5 wt. %, more preferably of less than 3 wt. %, still more preferably of less than 1 wt. %, and in particular 0 wt. %, based on the total weight of the antiperspirant cosmetic agent. "Free water" within the meaning of the present invention thus shall be understood to mean water that is different from constitutional water, hydration water or similarly molecularly bound water present in the components used, in particular of the antiperspirant aluminum salts.

Surprisingly, it was found that significantly fewer textile discolorations and/or textile stains occur if the antiperspirant cosmetic agents used according to the invention include free water in an amount of 15 to 96 wt. %, based on the total weight of the antiperspirant cosmetic agent. In a particularly preferred embodiment of the present invention, the antiperspirant cosmetic agent used according to the invention thus includes free water in a total amount of 15 to 96 wt. %, especially 25 to 80 wt. %, preferably 30 to 70 wt. %, and in particular 40 to 60 wt. %, based on the total weight of the antiperspirant cosmetic agent.

The antiperspirant cosmetic agents used according to the invention are preferably present as suspensions of the undissolved antiperspirant aluminum salt in the cosmetic oil that is liquid at 20° C. and 1,013 hPa.

In a further preferred form of administration, the antiperspirant cosmetic agent used according to the invention is present as a water-in-oil emulsion. This may be in particular a sprayable water-in-oil emulsion, which can be sprayed by way of a propellant. In this connection, it is preferred if the polysaccharide is used in the antiperspirant cosmetic agent that is used according to the invention, which is present in the form of a water-in-oil emulsion, in a total amount of 0.05 to 8 wt. %, especially 0.1 to 7 wt. %, preferably 0.3 to 5 wt. %, more preferably 0.5 to 3 wt. %, still more preferably 0.8 to 2.5 wt. %, and in particular 1 to 2 wt. %, based on the total weight of the antiperspirant cosmetic agent.

It may also be provided within the scope of the present invention that the antiperspirant cosmetic agent used according to the invention is present as an oil-in-water emulsion. In this case, the agent that is used according to the invention is preferably sprayed as a propellant-free pump spray or squeeze spray or is applied as a roll-on. In this connection, it is preferred if the polysaccharide is used in the antiperspirant cosmetic agent that is used according to the invention, which is present in the form of an oil-in-water emulsion, in a total amount of 0.05 to 8 wt. %, especially 0.1 to 7 wt. %, preferably 0.3 to 5 wt. %, more preferably 0.5 to 3 wt. %, still more preferably 0.8 to 2.5 wt. %, and in particular 1 to 2 wt. %, based on the total weight of the antiperspirant cosmetic agent.

According to the invention, it may furthermore be provided that the antiperspirant cosmetic agent used according to the invention is present as an aqueous, aqueous-alcoholic or aqueous-glycolic solution.

According to a preferred embodiment of the present invention, the antiperspirant cosmetic agent used according to the invention includes ethanol in a total amount of 1 to 50 wt. %, especially 5 to 40 wt. %, preferably 7 to 35 wt. %, and in particular 10 to 30 wt. %, based on the total weight of the antiperspirant cosmetic agent. However, it may also be provided that ethanol is used in the antiperspirant cosmetic agent that is used according to the invention in a total amount of 10 to 95 wt. %, especially 15 to 90 wt. %, preferably 20 to 87 wt. %, more preferably 30 to 85 wt. %, and in particular 40 to 80 wt. %, based on the total weight of the antiperspirant cosmetic agent.

The antiperspirant cosmetic agents used according to the invention can be applied using different methods. According to a preferred embodiment, the antiperspirant cosmetic agent used according to the invention is formulated as a spray application. The spray application is carried out using a spraying device, which in a container contains a filling composed of the antiperspirant cosmetic agent used according to the invention in liquid, viscous-flowable, suspension or powder form. The filling can be a pressurized propellant (pressurized cans, pressurized containers, aerosol dispensers), or it can be a pump atomizer that contains no propellant gas and is to be operated mechanically (pump sprays, squeeze bottle). The containers comprise a withdrawal device, preferably in the form of valves, allowing the content to be withdrawn in the form of a mist, smoke, foam, powder, paste or fluid jet. Especially cylindrical vessels made of metal (aluminum, tinplate, volume preferably no more than 1,000 mol), protected or shatterproof glass or plastic (volume preferably no more than 220 ml) or shattering glass or plastic (volume preferably 50 to 400 ml) can be used as containers for the spraying devices. Cream-like, gel-like, pasty and liquid agents used according to the invention can be packaged in pump, spray or squeeze dispensers, for example, in particular also in multi-chamber pump, multi-chamber spray, or multi-chamber squeeze dispensers. The packaging for the agents used according to the invention can be opaque, but may also be transparent or translucent.

The antiperspirant cosmetic agent used according to the invention is preferably formulated as a stick, soft solid, cream, roll-on, dibenzylidene alditol-based gel, or loose or compact powder. The formulation of the antiperspirant cosmetic agents used according to the invention in a particular form of administration, such as an antiperspirant roll-on or an antiperspirant stick or an antiperspirant gel, is preferably dependent on the requirements of the intended purpose. Depending on the intended purpose, the antiperspirant cosmetic agents used according to the invention can thus be present in solid, semi-solid, liquid, disperse, emulsified, suspended, gel-like, multi-phase or powder form. The term 'liquid' within the meaning of the present invention also covers any type of solid dispersions in liquids. Furthermore, multi-phase antiperspirant cosmetic agents used according to the invention within the meaning of the present invention shall be understood to mean agents which contain at least two different phases having a phase separation and in which the phases may be disposed horizontally, which is to say on top of each other, or vertically, which is to say next to each other.

The application can take place by way of a roller ball applicator, for example. Such rollers comprise a ball that is mounted in a ball bed and can be moved by motion across a surface. The ball picks up a small amount of the antiperspirant agent to be distributed in this process and delivers the same to the surface to be treated. As described above, the packaging for the agents used according to the invention can be opaque, transparent or translucent.

Moreover, it is also possible to apply the antiperspirant cosmetic agents used according to the invention by way of a solid stick.

The antiperspirant cosmetic agents used according to the invention can additionally include further auxiliary substances. The antiperspirant cosmetic agents used according to the invention preferably comprise at least one further auxiliary substance, selected from the group consisting of (i) emulsifiers and/or surfactants; (ii) hydrogel-forming agents; (iii) chelating agents; (iv) active deodorant ingredients; (v) monohydric and/or polyhydric alcohols and/or polyethylene glycols; (vi) skin-cooling active ingredients; (vii) propellants; (viii) inorganic lipophilic thickeners; and (ix) the mixtures thereof.

Preferably suited emulsifiers and surfactants according to the invention are selected from anionic, cationic, nonionic, amphoteric, in particular ampholytic and zwitterionic, emulsifiers and surfactants. Surfactants are amphiphilic (bifunctional) compounds, which are composed of at least one hydrophobic molecule part and at least one hydrophilic molecule part. The hydrophobic group is preferably a hydrocarbon chain having 8 to 28 carbon atoms, which can be saturated or unsaturated, linear or branched. This $C_8$ to $C_{28}$ alkyl chain is particularly preferably linear.

Anionic surfactants shall be understood to mean surfactants carrying exclusively anionic charges; they include carboxyl groups, sulfonic acid groups, or sulfate groups, for example. Particularly preferred anionic surfactants are alkyl sulfates, alkyl ether sulfates, acyl glutamates, and $C_{8-24}$ carboxylic acids, and the salts thereof, known as soaps.

Cationic surfactants shall be understood to mean surfactants carrying exclusively cationic charges; they include quaternary ammonium groups, for example. Cationic surfactants of the quaternary ammonium compound, esterquat and amidoamine types are preferred. Preferred quaternary ammonium compounds are ammonium halides and the imidazolium compounds known under the INCI names Quaternium-27 and Quaternium-83. Other cationic surfactants that can be used according to the invention are the quaternized protein hydrolysates. Preferred esterquats are quaternized ester salts of fatty acids with triethanolamine, quaternized ester salts of fatty acids with diethanol alkylamines, and quaternized ester salts of fatty acids with 1,2-dihydroxypropyl dialkylamines.

Amphoteric surfactants are divided into ampholytic surfactants and zwitterionic surfactants. Ampholytic surfactants are understood to include those surface active compounds that carry both acidic (—COOH or —SO$_3$H groups, for example) and basic hydrophilic groups (amino groups, for example) and can exhibit acidic or basic behavior, depending on the conditions. A person skilled in the art considers zwitterionic surfactants to be surfactants that carry both a negative charge and a positive charge in the same molecule. Examples of preferred zwitterionic surfactants are betaines, N-alkyl-N,N-dimethylammonium glycinates, N-acyl-aminopropyl-N,N-dimethylammonium glycinates, and 2-alkyl-3-carboxymethyl-3-hydroxyethyl imidazolines, each having 8 to 24 carbon atoms in the alkyl group. Examples of preferred ampholytic surfactants are N-alkyl glycines, N-alkylaminopropionic acids, N-alkylaminobutytic acids, N-alkyliminodipropionic acids, N-hydroxyethyl-N-alkylamidopropyl glycines, N-alkyl taurines, N-alkyl sarcosines, 2-alkylaminopropionic acids, and alkylaminoacetic acids, each having 8 to 24 carbon atoms in the alkyl group.

The compositions used according to the invention formulated as emulsions, in particular as oil-in-water emulsions, preferably include at least one nonionic oil-in-water emulsifier having an HLB value of more than 7 to 20. These are emulsifiers that are generally known to a person skilled in the art, as they are listed in Kirk-Othmer, "Encyclopedia of Chemical Technology", 3rd edition, 1979, Volume 8, pages 913-916, for example. For ethoxylated products, the HLB value is calculated according to formula HLB=(100-L):5, where L is the weight proportion of the lipophilic groups, which is to say of the fatty alkyl or fatty acyl groups, in the ethylene oxide adducts, expressed in percent by weight. In this connection, it may be preferred according to the invention if furthermore a water-in-oil emulsifier having an HLB value of greater than 1.0 and less than/equal to 7.0 is used. Suitable nonionic oil-in-water emulsifiers and suitable nonionic water-in-oil emulsifiers within the scope of the present invention are described in the German unexamined patent application DE 10 2006 004 957 A1, for example.

It may furthermore be advantageous to add at least one chelating agent to the antiperspirant cosmetic agents used according to the invention, which is selected from ethylenediaminetetraacetic acid (EDTA) and the salts thereof, and from nitrilotriacetic acid (NTA), and mixtures of these substances, in a total amount of 0.01 to 0.5 wt. %, especially 0.02 to 0.3 wt. %, in particular 0.05 to 0.1 wt. %, based on the total weight of the antiperspirant cosmetic agent.

The antiperspirant action of the antiperspirant cosmetic agents used according to the invention can be further increased if at least one active deodorant ingredient is used in a total amount of 0.0001 to 40 wt. %, especially 0.2 to 20 wt. %, preferably 1 to 15 wt. %, and in particular 1.5 to 5 wt. %, based on the total weight of the antiperspirant cosmetic agent. If ethanol is used in the cosmetic agents used according to the invention, this is not considered an active deodorant ingredient within the scope of the present invention, but a component of the carrier. Preferred active deodorant ingredients according to the invention are selected from the group consisting of (i) silver salts; (ii) aromatic alcohols, in particular 2-benzylheptane-1-ol and mixtures of 2-benzylheptane-1-ol and phenoxyethanol; (iii) 1,2-alkane diols having 5 to 12 carbon atoms, in particular 3-(2-ethylhexyloxy)-1,2-propane diol; (iv) triethyl citrates; (v) active ingredients against exoesterases, in particular against arylsulfatase, lipase, beta-glucuronidase and cystathionine ß-lyase; (vi) cationic phospholipids; (vii) odor absorbers, in particular silicates, such as montmorillonite, kaolinite, illite, beidellite, nontronite, saponite, hectorite, bentonite, smectite, and talcum, zeolites, zinc ricinoleate, cyclodextrins; (viii) deodorizingly acting ion exchangers; (ix) antimicrobial substances; (x) prebiotically active components; and (xi) mixtures of these active deodorant ingredients.

Preferred antiperspirant cosmetic agents used according to the invention furthermore include at least one water-soluble polyhydric C$_{2-9}$ alkanol having 2 to 6 hydroxyl groups and/or at least one water-soluble polyethylene glycol having 3 to 50 ethylene oxide units, and mixtures thereof. These include the active deodorant ingredients not mentioned above in the form of 1,2-alkane diols. Preferred alkanols are selected from 1,2-propylene glycol, 2-methyl-1,3-propanediol, glycerol, 1,2-butylene glycol, 1,3-butylene glycol, 1,4-butylene glycol, pentylene glycols such as 1,2-pentanediol and 1,5-pentanediol, hexanediols such as 1,2-hexanediol and 1,6-hexanediol, hexanetriols such as 1,2,6-hexanetriol, 1,2-octanediol, 1,8-octanediol, dipropylene glycol, tripropylene glycol, diglycerol, triglycerol, erythritol, sorbitol, cis-1,4-dimethylol cyclohexane, trans-1,4-dimethylol cyclohexane, arbitrary isomer mixtures of cis- and trans-1,4-dimethylol cyclohexane, and mixtures of the aforementioned substances. Suitable water-soluble polyethylene glycols are selected from PEG-3, PEG-4, PEG-6, PEG-7, PEG-8, PEG-9, PEG-10, PEG-12, PEG-14, PEG-16, PEG-18 and PEG-20, and mixtures thereof, PEG-3 to PEG-8 being preferred.

According to a further embodiment of the present invention, the antiperspirant cosmetic agents used according to the invention furthermore include at least one skin-cooling active ingredient. Suitable skin-cooling active ingredients according to the invention are, for example, menthol, isopulegol and menthol derivatives, such as menthyl lactate, menthyl glycolate, menthyl ethyl oxamate, menthyl pyrrolidone carboxylic acid, menthyl methyl ether, menthoxypropanediol, menthone glycerin acetal (9-methyl-6-(1-methylethyl)-1,4-dioxaspiro(4.5)decane-2-methanol), monomenthyl succinate, 2-hydroxymethyl-3,5,5-trimethylcyclohexanol, and 5-methyl-2-(1-methylethyl)cyclohexyl-N-ethyloxamate. Menthol, isopulegol, menthyl lactate, menthoxypropanediol, menthylpyrrolidone carboxylic acid and 5-methyl-2-(1-methylethyl)cyclohexyl-N-ethyloxamate and mixtures of these substances, in particular mixtures of menthol and menthyl lactate, menthol, menthol glycolate and menthyl lactate, menthol and menthoxypropanediol, or menthol and isopulegol, are preferred as skin-cooling active ingredients.

It may furthermore be provided that a propellant is present in the antiperspirant cosmetic agents used according to the invention. In this case, they are formulated as a propellant gas-driven aerosol. Preferred propellants (propellant gases) are propane, propene, n-butane, iso-butane, iso-butene, n-pentane, pentene, iso-pentane, iso-pentene, methane, ethane, dimethylether, nitrogen, air, oxygen, nitrous oxide, 1,1,1,3-tetrafluoroethane, heptafluoro-n-propane, perfluoroethane, monochlorodifluoromethane, 1,1-difluoroethane, tetrafluoropropene, and more particularly both individually and in the mixtures thereof. It is also possible to advantageously use hydrophilic propellants, such as carbon dioxide, within the meaning of the present invention if the proportion of hydrophilic gases is selected to be low, and lipophilic propellant (such as propane/butane) is present in excess. Propane, n-butane, iso-butane and mixtures of these propellants are particularly preferred. It has been shown that the use of n-butane as the sole propellant may be particularly preferred according to the invention. The total amount of propellants is 20 to 95 wt. %, especially 30 to 85 wt. %, in particular 40 to 75 wt. %, in each case based on the total weight of the antiperspirant, composed of the antiperspirant cosmetic agent used according to the invention and the propellant. In this connection, it may also be provided that the total amount of propellants is 1 to 95 wt. %, especially 2 to 85 wt. %, in particular 3 to 75 wt. %, in each case based on the total weight of the antiperspirant, composed of the antiperspirant cosmetic agent used according to the invention and the propellant.

Furthermore, inorganic lipophilic thickeners can be used according to the invention as auxiliary substances. The at least one antiperspirant aluminum salt is preferably suspended undissolved in at least one cosmetic oil that is liquid at 20° C. and 1,013 hPa. To improve applicability, at least one inorganic lipophilic thickener can also be added to this suspension as a suspending aid. Preferred inorganic lipophilic thickeners according to the invention are selected from hydrophobized clay minerals and fumed silica.

In a preferred embodiment, the antiperspirant cosmetic agents used according to the invention are characterized by being formulated as water-in-oil emulsions and containing—based on the total weight of the antiperspirant cosmetic agent according to the invention—
- at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;
- at least one polysaccharide in a total amount of 0.05 to 8 wt. %, especially 0.1 to 7 wt. %, preferably 0.3 to 5 wt. %, more preferably 0.5 to 3 wt. %, still more preferably 0.8 to 2.5 wt. %, and in particular 1 to 2 wt. %;
- 12 to 90% by weight, especially 25 to 55% by weight, preferably 30 to 50% by weight, and in particular 35 to 45 wt. % water;
- at least one emulsifier; and
- at least one substance selected from the group consisting of cosmetic oils that are liquid at 20° C. and 1,013 hPa, odorous substances and waxes.

In a further preferred embodiment, the antiperspirant cosmetic agents used according to the invention are characterized by being formulated as oil-in-water emulsions and containing—based on the total weight of the antiperspirant cosmetic agent according to the invention—
- at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;
- at least one polysaccharide in a total amount of 0.05 to 8 wt. %, especially 0.1 to 7 wt. %, preferably 0.3 to 5 wt. %, more preferably 0.5 to 3 wt. %, still more preferably 0.8 to 2.5 wt. %, and in particular 1 to 2 wt. %;
- 15 to 90% by weight, especially 25 to 55% by weight, preferably 30 to 50% by weight, and in particular 35 to 45 wt. % water;
- at least one emulsifier; and
- at least one substance selected from the group consisting of cosmetic oils that are liquid at 20° C. and 1,013 hPa, odorous substances and waxes.

A further preferred embodiment of the present invention comprises antiperspirant cosmetic agents used according to the invention, which are characterized by containing—based on the total weight of the antiperspirant cosmetic agent according to the invention—
- at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;
- at least one polysaccharide in a total amount of 0.05 to 8 wt. %, especially 0.1 to 7 wt. %, preferably 0.3 to 5 wt. %, more preferably 0.5 to 3 wt. %, still more preferably 0.8 to 2.5 wt. %, and in particular 1 to 2 wt. %;
- 15 to 90% by weight, especially 25 to 80% by weight, preferably 30 to 75% by weight, and in particular 40 to 60 wt. % water.

A further preferred embodiment of the present invention comprises antiperspirant cosmetic agents used according to the invention, which are characterized by containing—based on the total weight of the antiperspirant cosmetic agent according to the invention—
- at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;
- at least one polysaccharide in a total amount of 0.05 to 8 wt. %, especially 0.1 to 7 wt. %, preferably 0.3 to 5 wt. %, more preferably 0.5 to 3 wt. %, still more preferably 0.8 to 2.5 wt. %, and in particular 1 to 2 wt. %;
- 15 to 90% by weight, especially 25 to 80% by weight, preferably 30 to 75% by weight, and in particular 40 to 60 wt. % water; and wherein the antiperspirant cosmetic agents used according to the invention have a dynamic viscosity in the range from 10 to 5000 mPas, especially from 100 to 1000 mPas, preferably from 200 to 800 mPas, measured by way of a Brookfield viscometer, RV 4 spindle, 20 s$^{-1}$, without Helipath, at 20° C. ambient temperature and 20° C. sample temperature.

A further preferred embodiment of the present invention comprises antiperspirant cosmetic agents used according to the invention, which are characterized by containing—based on the total weight of the antiperspirant cosmetic agent according to the invention—
- at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;
- at least one polysaccharide in a total amount of 0.05 to 8 wt. %, especially 0.1 to 7 wt. %, preferably 0.3 to 5 wt. %, more preferably 0.5 to 3 wt. %, still more preferably 0.8 to 2.5 wt. %, and in particular 1 to 2 wt. %;
- 15 to 90% by weight, especially 25 to 80% by weight, preferably 30 to 75% by weight, and in particular 40 to 60 wt. % water; and wherein the antiperspirant cosmetic agents used according to the invention have a dynamic viscosity in the range from 5000 to 600000 mPas, especially from 4000 to 550000 mPas, preferably from 3000 to 500000 mPas, measured by way of a Brookfield viscometer, RV 4 spindle, 20 s$^{-1}$, without Helipath, at 20° C. ambient temperature and 20° C. sample temperature.

In another preferred embodiment, the antiperspirant cosmetic agents used according to the invention are characterized by being formulated as water-in-oil emulsions and containing—based on the total weight of the antiperspirant cosmetic agent according to the invention—
- at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;
- at least one polysaccharide in a total amount of 0.05 to 8 wt. %, especially 0.1 to 7 wt. %, preferably 0.3 to 5 wt.

%, more preferably 0.5 to 3 wt. %, still more preferably 0.8 to 2.5 wt. %, and in particular 1 to 2 wt. %;

15 to 75% by weight, especially 25 to 60% by weight, preferably 30 to 55% by weight, and in particular 35 to 50 wt. % water.

In a further preferred embodiment, the antiperspirant cosmetic agents used according to the invention are characterized by being formulated as oil-in-water emulsions and containing—based on the total weight of the antiperspirant cosmetic agent according to the invention— at least one antiperspirant aluminum salt in a total amount of 2 to 75 wt. %, especially 3 to 70 wt. %, preferably 4 to 65 wt. %, more preferably 5 to 55 wt. %, still more preferably 8 to 40 wt. %, and in particular 10 to 30 wt. %;

at least one polysaccharide in a total amount of 0.05 to 8 wt. %, especially 0.1 to 7 wt. %, preferably 0.3 to 5 wt. %, more preferably 0.5 to 3 wt. %, still more preferably 0.8 to 2.5 wt. %, and in particular 1 to 2 wt. %;

15 to 90% by weight, especially 25 to 80% by weight, preferably 30 to 75% by weight, and in particular 40 to 60 wt. % water and.

The present invention further relates to a method for preventing and/or reducing textile discolorations and/or textile stains, wherein the method comprises the following method steps:

(a) producing an antiperspirant cosmetic agent by mixing an antiperspirant aluminum salt with at least one polysaccharide and optionally further ingredients and optionally propellants;

(b) applying the antiperspirant cosmetic agent to the skin, in particular to the skin of the axilla;

(c) wearing a piece of textile clothing over the treated skin; and (d) washing the piece of textile clothing, in particular washing the piece of textile clothing multiple times, wherein after washing, in particular after multiple instances of washing, no or decreased textile discolorations and/or textile stains occur.

What was said with respect to the use according to the invention of polysaccharides in antiperspirant cosmetic agents and the use according to the invention of antiperspirant cosmetic agents for reducing and/or preventing textile discolorations and/or textile stains applies, mutatis mutandis, to the method.

The following examples describe the present invention in more detail, without limiting it to these examples.

EXAMPLES

1. Textile Discoloration and/or Textile Stains

1.1 Test Products Containing Volatile Oils in the Oil Phase

Test product V-I that was produced was an oily suspension, composed of 33.3 wt. % activated aluminum chlorohydrate, 49.4 wt. % cyclopentasiloxane, 6.67 wt. % isopropyl myristate, 2.53 wt. % Bentone 38 V CG, 0.867 wt. % propylene carbonate, 6.67 wt. % perfume 233385 Bossa Nova, and 0.500 wt. % 252479 Incap. Frag. No. 174917/ENC/200. Such a suspension is, among other things, representative of anhydrous antiperspirant roll-ons, anhydrous antiperspirant wax sticks, and anhydrous antiperspirant sprays.

To produce the test products according to the invention, 50 grams of the above mixture V-I is mixed in each case with 2 wt. % of a polysaccharide. The respectively used polysaccharides for producing the test products according to the invention are listed in Table 1 below.

TABLE 1

| Test products according to the invention | | |
|---|---|---|
| No. | Polysaccharide | |
| E-I | methyl hydroxypropyl cellulose (Methocel E4M) | |
| E-II | cetyl hydroxyethylcellulose (Natrosol plus 330) | |
| E-III | microcrystalline cellulose (Viavapur 105) | |

0.3 grams of the respective product V-I, E-I, E-II, and E-III were applied directly to a 10×10 cm² large piece of light blue cotton fabric (polo jersey, woven), which was sewn to a waffle pique towel. After a waiting period of one hour, 1 ml of an artificial sweat mixture ($MgCl_2$, $CaCl_2$, KCl, NaCl, $Na_2SO_4$, $NaH_2PO_4$, glycine, glucose, lactic acid, urea; pH 5.2) was applied, and after a 24-hour waiting period (aging), the textile was washed using a standardized washing process customary for households (Miele W 1714) and machine-dried (Miele T 7644C). The washing conditions are indicated in Table 2 below.

TABLE 2

| Parameters of the washing process | |
|---|---|
| Load: | 3.5 kg |
| Amount of water: | 17 L |
| Temperature: | 40° C. |
| Time for main washing cycle: | 1 h |
| Prewash: | without |
| Rinsing: | 4 x |
| Detergent: | Spee Color Gel (Batch: HH06.1.1UWM1.08:58) |
| Net weight detergent: | 75 ml (70 g) |
| Softener: | without |
| Dryer program: | extra dry - cotton |

The product application and washing process were repeated with the same textile a total of eight times (corresponds to 8 soiling/washing cycles). The evaluation of the textile soiling was carried out visually by trained laboratory technicians based on reference examples. The scale ranged from 0 (no stains) to 4 (very strong staining). The evaluation was carried out immediately after the washing series was completed. The results indicated in Table 3 were obtained.

TABLE 3

| Results of the visual residue evaluation after 8 soiling/washing cycles | | |
|---|---|---|
| Product | white | greasy |
| V-I | 1 | 1 |
| E-I | 0.7 | 0 |
| E-II | 0.5 | 0.5 |
| E-III | 0.5 | 0.5 |

Compared to comparison formulation V-I not containing the addition of a special polysaccharide, the test formulations E-I, E-II, and E-III according to the invention, which include 2 wt. % of a special polysaccharide, exhibit a considerably reduced formation of white and greasy spots on light blue textile material.

1.2 Test Products Containing Non-Volatile Oils in the Oil Phase

Test product V-II that was produced was an oily suspension, composed of 14.3 wt. % activated aluminum chlorohydrate, 68.0 wt. % 2-ethylhexyl palmitate, 5.36 wt. % triethyl citrate, 3.93 wt. % Bentone 38 V CG, 1.29 wt. % propylene carbonate, and 7.14 wt. % perfume TEU-E-1451 Padma won. Such a suspension is, among other things, representative of anhydrous antiperspirant roll-ons, anhydrous antiperspirant wax sticks, and anhydrous antiperspirant sprays.

To produce the test products according to the invention, 50 grams of the above mixture V-II is mixed in each case with 2 wt. % of a polysaccharide. The respectively used polysaccharides for producing the test products according to the invention are listed in Table 4 below.

TABLE 4

Test products according to the invention

| No. | Polysaccharide |
|---|---|
| E-IV | methyl hydroxypropyl cellulose (Methocel E4M) |
| E-V | cetyl hydroxyethylcellulose (Natrosol plus 330) |
| E-VI | microcrystalline cellulose (Viavapur 105) |

0.3 grams of the respective product V-II, E-VI, E-V, and E-VI were applied directly to a 10×10 cm² large piece of light blue cotton fabric (polo jersey, woven), which was sewn to a waffle pique towel. After a waiting period of one hour, 1 ml of an artificial sweat mixture (MgCl$_2$, CaCl$_2$, KCl, NaCl, Na$_2$SO$_4$, NaH$_2$PO$_4$, glycine, glucose, lactic acid, urea; pH 5.2) was applied, and after a 24-hour waiting period (aging), the textile was washed using a standardized washing process customary for households (Miele W 1714) and machine-dried (Miele T 7644C) The washing conditions are indicated in Table 5 below.

TABLE 5

Parameters of the washing process

| Load: | 3.5 kg |
|---|---|
| Amount of water: | 17 L |
| Temperature: | 40° C. |
| Time for main washing cycle: | 1 h |
| Prewash: | without |
| Rinsing: | 4 x |
| Detergent: | Spee Color Gel (Batch: HH06.1.1UWM1.08:58) |
| Net weight detergent: | 75 ml (70 g) |
| Softener: | without |
| Dryer program: | extra dry - cotton |

The product application and washing process were repeated with the same textile a total of eight times (corresponds to 8 soiling/washing cycles). The evaluation of the textile soiling was carried out visually by trained laboratory technicians based on reference examples. The scale ranged from 0 (no stains) to 4 (very strong staining). The evaluation was carried out immediately after the washing series was completed. The results indicated in Table 6 were obtained.

TABLE 6

Results of the visual residue evaluation after 8 soiling/washing cycles

| Product | white | greasy |
|---|---|---|
| V-II | 0 | 4 |
| E-IV | 0 | 3 |
| E-V | 0 | 3 |
| E-VI | 0 | 3 |

Compared to comparison formulation V-II not containing the addition of a special polysaccharide, the test formulations E-IV, E-V, and E-VI according to the invention, which include 2 wt. % of a special polysaccharide, exhibit a considerably reduced formation of greasy spots on light blue textile material.

2. Formulation Examples

The following formulation examples are intended to illustrate the subject matter of the invention, without thereby limiting the invention to these examples. The polysaccharide used in the examples below is preferably a hydroxyethyl cellulose, a hydroxyethyl methyl cellulose, a methylcellulose, a hydroxypropyl methyl cellulose, a cetyl hydroxyethylcellulose or a mixture of the aforementioned chemically modified celluloses. Furthermore, preferably a microcrystalline cellulose and the mixture thereof with the above-mentioned chemically modified celluloses is used.

Antiperspirant Cosmetic Agents Used According to the Invention (Quantity Information in Wt. %)

| | 1 | 2 | 3 | 4 | 5 | 6 |
|---|---|---|---|---|---|---|
| Hydrogenated castor oil | — | — | — | 1.5 | 1.5 | 1.5 |
| Stearyl alcohol | 24.0 | 24.0 | 24.0 | 18 | 18 | 18 |
| Novata AB | — | — | — | 4 | 4 | 4 |
| Al—Zr pentachlorohydrex Gly | 22.0 | 22.0 | 22.0 | 17.6 | 17.6 | 17.6 |
| Polysaccharide | 2.0 | 1.5 | 1.0 | 1.75 | 1.25 | 2.0 |
| PPG-14 butyl ether | 10.0 | 10.0 | 10.0 | 15.3 | 15.3 | 15.3 |
| Hardened castor oil (e.g., Cutina FIR) | 3.0 | 3.0 | 3.0 | — | — | — |
| Myristyl myristate | 1.5 | 1.5 | 1.5 | — | — | — |
| DL menthol | 0.2 | 0.2 | 0.2 | — | — | — |
| Eucalyptol | 0.2 | 0.2 | 0.2 | — | — | — |
| Anethol | 0.2 | 0.2 | 0.2 | — | — | — |
| Silica dimethyl silylate | 0.3 | 0.3 | 0.3 | — | — | — |
| Talcum | — | — | — | 3 | 3 | 3 |
| Emulgin B1 | — | — | — | 3 | 3 | 3 |
| Perfume | 2.0 | 2.0 | 2.0 | 1 | 1 | 1 |
| Cyclomethicone (at least 95 wt. % cyclepentasiloxane) | up to 100 | up to 100 | up to 100 | up to 100 | up to 100 | up to 100 |

Antiperspirant Cosmetic Agents Used According to the Invention in the Form of an Oil-in-Water Emulsion (Quantity Information in Wt. %)

| | 7 | 8 |
|---|---|---|
| Cutina ® AGS | 2.5 | 2.5 |
| Cutina ® FS45 | 3.5 | 3.5 |
| Eumulgin ® B2 | 0.8 | 0.8 |
| Eumulgin ® B3 | 0.8 | 0.8 |
| Diisopropyl adipate | 6.0 | 6.0 |
| Novata ® AB | 4.0 | 4.0 |
| Cutina ® CP | 5.0 | 5.0 |
| Cutina ® HR | 4.0 | 4.0 |
| Kester Wax K62 | 5.0 | 5.0 |
| Locron ® L (ACH solution 50%) | 40 | 40 |
| Talcum Pharma G | 10 | 10 |
| Perfume | 1.2 | 1.2 |
| 2-benzylheptane-1-ol | — | 0.3 |
| Sensiva SC 50 | 0.6 | 0.6 |
| Polysaccharide | 2.0 | 3.0 |
| 1,2-propanediol | 10 | 10 |
| Water, demineralized | up to 100 | up to 100 |

Antiperspirant Cosmetic Agents Used According to the Invention in the Form of a Microemulsion (Information in Wt. %)

|  | 9 | 10 | 11 | 12 |
| --- | --- | --- | --- | --- |
| Plantaren ® 1200 | 1.7 | 1.7 | — | — |
| Plantaren ® 2000 | 1.1 | 1.4 | 2.4 | 2.4 |
| Glycerol monooleate | 0.71 | 0.71 | — | — |
| Dioctyl ether | 4.0 | 4.0 | 0.090 | 0.090 |
| Octyldodecanol | 1.0 | 1.0 | 0.020 | 0.020 |
| Perfume oil | 1.0 | 1.0 | 1.0 | 1.0 |
| Aluminum chlorohydrate | 8.0 | 5.0 | 5.0 | 5.0 |
| 1,2-propylene glycol | 5.0 | 5.0 | — | — |
| Glycerol | — | — | 5.0 | 5.0 |
| 2-benzylheptane-1-ol | 0.50 | — | — | — |
| Triethyl citrate | — | 0.50 | 0.50 | 0.50 |
| Triclosan | 0.10 | — | — | — |
| Polysaccharide | 1.0 | 2.0 | 2.5 | 0.5 |
| Water | up to 100 | up to 100 | up to 100 | up to 100 |

Antiperspirant Cosmetic Agents Used According to the Invention in the Form of Roll-Ons (Quantity Information in Wt. %)

|  | 13 | 14 | 15 | 16 |
| --- | --- | --- | --- | --- |
| Ethanol 96% (DEP denatured) | 30 | 30 | 28 | 28 |
| Mergital ® CS 11 | 2.0 | 2.0 | — | — |
| Eumulgin ® B3 | 2.0 | 2.0 | 2.0 | 2.0 |
| Eumulgin ® B1 | — | — | 2.0 | 2.0 |
| Aluminum chlorohydrate 50% (Locron L) | 20 | 20 | 16 | 16 |
| Hydroxyethyl cellulose | 0.50 | 0.50 | 0.30 | 0.30 |
| Polysaccharide | 2.5 | 0.50 | 2.0 | 1.5 |
| EDTA | — | — | — | 0.050 |
| Cocamidopropyl PG dimonium chloride phosphate | 0.20 | — | — | — |
| Perfume oil | 0.80 | 0.80 | 1.0 | 1.0 |
| Water | up to 100 | up to 100 | up to 100 | up to 100 |

Antiperspirant Cosmetic Agents Used According to the Invention in the Form of a Water-in-Oil Emulsion (Quantity Information in Wt. %)

|  | 21 | 22 |
| --- | --- | --- |
| Aluminum chlorohydrate 50% in water (Locron L) | 35.6 | 35.6 |
| 1,2-propylene glycol | 13.0 | 13.0 |
| Cyclohexasiloxane | 6.00 | 6.00 |
| Finsolv TN | 8.00 | 8.00 |
| Abil EM 90 | 1.20 | 1.20 |
| Polyethylene wax (MW = 500 g/mol, melting pt = 83 to 91° C.) | 10.0 | 10.0 |
| Polyalphaolefin wax (MW = 1800 g/mol, melting pt = 41° C.) | 0.100 | 0.100 |
| Polysaccharide | 2.00 | 0.500 |
| EDTA | — | 0.05000 |
| Water | 25.0 | 25.0 |
| Perfume | 1.00 | 1.00 |

Antiperspirant Cosmetic Agents Used According to the Invention (Quantity Information in Wt. %)

|  | 23 | 24 |
| --- | --- | --- |
| Cyclopentasiloxane | 14.0 | 14.0 |
| Abil EM 97 | 3.00 | 3.00 |
| Ethanol 96% | 10.0 | 10.0 |
| Aluminum chlorohydrate 50% in water (Locron L) | 40.0 | 40.0 |
| 1,2-propylene glycol | 20.3 | 20.3 |
| Water | 11.6 | 11.6 |
| Polysaccharide | 2.00 | 0.500 |
| EDTA | — | 0.0750 |
| Perfume | 1.00 | 1.00 |

Antiperspirant Cosmetic Agents Used According to the Invention (Quantity Information in Wt. %, Based on the Total Weight of the Propellant-Free Composition)

|  | 27 | 28 | 29 | 30 |
| --- | --- | --- | --- | --- |
| Aluminum chlorohydrate (ACH) | 28.6 | 14.29 | 32.11 | 28.57 |
| Bentone 38 V CG | 5.00 | 3.93 | 4.00 | 5.00 |
| Propylene carbonate | 1.50 | 0.71 | 1.50 | 1.80 |
| Fragrance | 7.14 | 6.50 | 5.00 | 6.50 |
| 2-ethylhexyl palmitate | — | 73.57 | — | — |
| Abil K 4 | 48.4 | — | — | — |
| Isopropyl myristate | 7.37 | — | 10.00 | 19.22 |
| Triethyl citrate | — | — | 10.5 | 19.2 |
| C10-C13 isoalkane | — | — | 35.39 | 19.21 |
| Polysaccharide | 2.00 | 1.00 | 1.50 | 0.500 |
| Water | up to 100 | up to 100 | up to 100 | up to 100 |

Exemplary compositions 27 to 30 were bottled in an aluminum spray can, optionally coated with epoxy-phenolic lacquer, at a weight ratio of the propellant (butane/propane/isobutane mixture) to the suspension of 80:20 and 85:15 and 60:40 and 90:10.

Antiperspirant Cosmetic Agents Used According to the Invention (Quantity Information in Wt. %, Based on the Total Weight of the Propellant-Free Composition)

|  | 31 | 32 | 33 |
| --- | --- | --- | --- |
| Aluminum chlorohydrate (ACH) | 33.0 | 33.0 | 33.0 |
| $C_{10}$ to $C_{13}$ isoalkane | 8.90 | 8.90 | 8.90 |
| Dow Corning ES-5227 DM | 1.40 | 1.40 | 1.40 |
| Isoceteth-20 | 0.500 | 0.500 | 0.500 |
| Dimethicone | 4.20 | 4.20 | 4.20 |
| Isopropyl myristate | 9.00 | 9.00 | 9.00 |
| 1,2-propanediol | 7.00 | 25.00 | 25.0 |
| Phenoxyethanol | 0.500 | 0.500 | 0.500 |
| Perfume | 2.50 | 2.50 | 2.50 |
| Polysaccharide | 2.00 | 0.500 | 1.50 |
| L-Menthol | 0.400 | 0.300 | — |
| trans-anethol | — | 0.300 | — |
| Eucalyptol | — | 0.300 | — |
| Water | up to 100 | up to 100 | up to 100 |

Exemplary compositions 31 to 33 were bottled in an aluminum spray can, optionally coated with epoxy-phenolic lacquer, at a weight ratio of the propellant (butane/propane/isobutane mixture) to the W/O suspension of 80:20 and 85:15 and 60:40 and 90:10.

Antiperspirant Cosmetic Agents Used According to the Invention in the Form of O/W Emulsions (Quantity Information in Wt. %)

|  | 34 | 35 | 36 |
| --- | --- | --- | --- |
| Aluminum chlorohydrate (ACH) | 13.0 | 13.0 | 13.0 |
| Potassium aluminum sulfate $KAl(SO_4)_2 \cdot 12H_2O$ | 1.50 | 1.50 | 1.50 |
| Talcum | 1.0 | — | — |
| Bentonite | — | 1.00 | — |
| Hectorite | — | — | 5.0 |
| Brij S 2 | 2.50 | 2.50 | 2.50 |
| Brij S 721 | 1.50 | 1.50 | 1.50 |
| Perfume | 1.10 | 1.10 | 1.10 |
| Arlamol E | 0.500 | 0.500 | 0.500 |
| Bisabolol | 0.100 | 0.100 | 0.100 |
| Dry Flo PC | 0.100 | 0.100 | 0.100 |
| Polysaccharide | 2.00 | 3.00 | 1.00 |

-continued

|  | 34 | 35 | 36 |
|---|---|---|---|
| Dow Corning 2501 Cosmetic Wax | 0.100 | 0.100 | 0.100 |
| Tocopheryl acetate | 0.100 | 0.100 | 0.100 |
| Water | up to 100 | up to 100 | up to 100 |

Antiperspirant Cosmetic Agents Used According to the Invention (Quantity Information in Wt. %, Based on the Total Weight of the Propellant-Free Composition)

|  | 37 | 38 | 39 | 40 |
|---|---|---|---|---|
| Aluminum chlorohydrate (ACH) | 33.0 | 33.0 | 33.0 | 33.0 |
| Cyclomethicone | 12.0 | 9.40 | — | — |
| $C_{10}$ to $C_{13}$ isoalkane | — | — | 9.40 | 8.90 |
| Dow Corning ES-5227 DM | — | 1.40 | 1.40 | 1.40 |
| Abil EM 90 | 3.00 | — | — | — |
| Brij IC 20 | — | — | — | 0.500 |

-continued

|  | 37 | 38 | 39 | 40 |
|---|---|---|---|---|
| Dimethicone | — | 4.20 | 4.20 | 4.20 |
| Isopropyl myristate | 9.00 | 9.00 | 9.00 | 9.00 |
| Polysaccharide | 2.50 | 1.00 | 3.00 | 0.500 |
| 1,2-propanediol | 7.00 | 7.00 | 7.00 | 7.00 |
| Phenoxyethanol | 0.500 | 0.500 | 0.500 | 0.500 |
| Perfume | 2.50 | 2.50 | 2.50 | 2.50 |
| Water | up to 100 | up to 100 | up to 100 | up to 100 |

Exemplary compositions 37 to 40 were bottled in an aluminum spray can, optionally coated with epoxy-phenolic lacquer, at a weight ratio of the propellant (butane/propane/isobutane mixture) to the W/O suspension of 80:20 and 85:15 and 60:40 and 90:10.

Antiperspirant Cosmetic Agents Used According to the Invention in the Form of W/O Emulsions (Quantity Information in Wt. %)

|  | 41 | 42 | 43 | 44 |
|---|---|---|---|---|
| Aluminum chlorohydrate 50% (Locron L) | 62.5 | 62.5 | 60.0 | 58.0 |
| Propylene glycol | 5.00 | 5.00 | 7.50 | 9.50 |
| $C_{12}$ to $C_{15}$ alkylbenzoate | 8.04 | 8.04 | 8.04 | 8.04 |
| Dimethicone 2 cst | 6.43 | 6.43 | 6.43 | 6.43 |
| Dimethicone 5 cst | 1.57 | 1.57 | 1.57 | 1.57 |
| Polyethylene | 10.2 | 11.7 | 9.70 | 12.2 |
| Abil EM 90 | 0.998 | 0.998 | 0.998 | 0.998 |
| Abil EM 97 | 1.22 | 1.22 | 1.22 | 1.22 |
| Polysaccharide | 2.50 | 1.00 | 3.00 | 0.500 |
| Synthetic wax | 0.100 | 0.100 | 0.100 | 0.100 |
| Perfume | 1.50 | 1.50 | 1.20 | 1.50 |

The Following Commercial Products were Used:

| Commercial product | INCI | Supplier/Manufacturer |
|---|---|---|
| Abil EM 90 | CETYL PEG/PPG-10/1 Dimethicone | Evonik |
| Abil EM 97 | Bis-PEG/PPG-14/14 Dimethicone, Cyclomethicone | Evonik |
| Abil K 4 | Cyclomethicone | Goldschmidt |
| Arlamol E | PPG-15 Stearyl ether | Croda |
| Bentone 38 V CG | Disteardimonium Hectorite | Elementis Specialities |
| Brij IC 20 | Isoceteth-20 | Croda |
| Brij S 2 | Steareth-2 | Croda |
| Brij S 721 | Steareth-21 | Croda |
| Cutina ® CP | Cetyl Palmitate | BASF |
| Cutina ® FS45 | Palmitic Acid, Stearic Acid | BASF |
| Cutina ® HR | Hydrogenated Castor Oil | BASF |
| Dow Corning ® 245 | Cyclopentasiloxan | Dow Corning |
| Dow Corning ® 2501 | Bis-PEG-18 Methyl ether dimethyl silane | Dow Corning |
| Dow Corning ES-5227 DM | Dimethicone, PEG/PPG-18/18 Dimethicone at a weight ratio of 3:1 | Dow Corning |
| Dry Flo PC | Aluminum Starch Octenylsuccinate | National Starch |
| Eumulgin ® B1 | Ceteareth-12 | BASF |
| Eumulgin ® B2 | Ceteareth-20 | BASF |
| Eumulgin ® B3 | Ceteareth-30 | BASF |
| Kester Wax K62 | Cetearyl Behenate | Koster Keunen |
| Finsolv TN | C12-15 Alkyl Benzoate | Innospec |
| Locron L (AS = 50%) | Aluminum Chlorohydrate | Clariant |
| Mergital ® CS 11 | Ceteareth-11 | BASF |
| Novata ® AB | Cocoglycerides (melting point 30-32° C.) | BASF |
| Plantaren ® 1200 | LAURYL GLUCOSIDE, approx. 50% AS | BASF |
| Plantaren ® 2000 | DECYL GLUCOSIDE, approx. 50% AS | BASF |
| Sensiva ® SC 50 | 2-Ethylhexylglycerin ether | Schülke & Mayr |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A method for preventing and/or reducing textile discolorations and/or textile stains, wherein the method comprises the following method steps:
    (a) producing an antiperspirant cosmetic agent by mixing an antiperspirant aluminum salt with at least one chemically modified polysaccharide and microcrystalline cellulose and optionally further ingredients and optionally propellants, wherein the antiperspirant aluminum salt is present in the cosmetic agent in an amount of 2 to 40 wt % based on the total weight of the cosmetic agent and the at least one chemically modified polysaccharide is present in an amount of 0.8 to 2.5 wt. % based on the total weight of the cosmetic agent;
    (b) applying the antiperspirant cosmetic agent to the skin;
    (c) wearing a piece of textile clothing over the treated skin; and
    (d) washing the piece of textile clothing, wherein after washing, no textile discolorations, no textile stains, decreased textile discolorations as compared to the same method using an antiperspirant cosmetic agent without the at least one chemically modified polysaccharide, or decreased textile stains as compared to the same method using an equivalent antiperspirant cosmetic agent without the at least one chemically modified polysaccharide wherein the at least one chemically modified polysaccharide is selected from the group consisting of $C_{1-10}$ alkyl cellulose, hydroxy $C_{2-10}$ alkyl methyl cellulose, hydroxy $C_{2-10}$ alkyl ethyl cellulose, hydroxy $C_{1-10}$ alkyl cellulose, carboxy $C_{1-10}$ alkyl cellulose, and $C_{6-30}$ alkyl hydroxyethyl cellulose, and mixtures thereof.

2. The method of claim 1, wherein the chemically modified polysaccharide includes chemically modified starches which are selected from the group consisting aluminum starch octenylsuccinate, sodium starch octenylsuccinate, calcium starch octenylsuccinate, dehydrated xanthan gum; and the mixtures thereof.

3. The method of claim 1, wherein the chemically modified polysaccharide is selected from the group consisting of methylcellulose, hydroxyethyl cellulose, hydroxyethyl methyl cellulose, hydroxypropyl cellulose, hydroxypropyl methyl cellulose, hydroxypropyl ethyl cellulose, carboxymethyl cellulose, and cetyl hydroxyethylcellulose.

4. The method of claim 1, wherein the antiperspirant aluminum salt is selected from the group consisting of aluminum chlorohydrate, aluminum sesquichlorohydrate, aluminum dichlorohydrate, aluminum hydroxide, potassium aluminum sulfate, aluminum bromohydrate, aluminum chloride, aluminum sulfate; aluminum chlorohydrex propylene glycol, aluminum chlorohydrex polyethylene glycol, aluminum propylene glycol complexes, aluminum sesquichlorohydrex propylene glycol, aluminum sesquichlorohydrex polyethylene glycol, aluminum propylene glycol dichlorohydrex, aluminum polyethylene glycol dichlorohydrex, aluminum undecylenoyl collagen amino acid, sodium aluminum lactate, sodium aluminum chlorohydroxy lactate, aluminum lipoamino acids, aluminum lactate, aluminum chlorohydroxy allantoinate, sodium aluminum chlorohydroxy lactate; and aluminum-zirconium trichlorohydrate, aluminum-zirconium tetrachlorohydrate, aluminum-zirconium pentachlorohydrate, aluminum-zirconium octachlorohydrate; aluminum-zirconium propylene glycol complexes, aluminum-zirconium trichlorohydrex glycine, aluminum-zirconium tetrachlorohydrex glycine, aluminum-zirconium pentachlorohydrex glycine, aluminum-zirconium octachlorohydrex glycine; and the mixtures thereof.

5. The method of claim 1, wherein weight ratio of the antiperspirant aluminum salt to the polysaccharide is from 40:1 to 19:1.

6. The method of claim 1, wherein weight ratio of the antiperspirant aluminum salt to the polysaccharide is from 9:1 to 12:1.

7. The method of claim 1, wherein the antiperspirant cosmetic agent further comprises at least one odorous substance a total amount of 0.00001 to 10 wt. % based on the total weight of the antiperspirant cosmetic agent.

8. The method of claim 1, wherein the antiperspirant cosmetic agent further comprises at least one wax in a total amount of 0.01 to 20 wt. % based on the total weight of the antiperspirant cosmetic agent.

9. The method of claim 1, further comprising 1 to 50 wt. % ethanol based on the total weight of the antiperspirant cosmetic agent.

* * * * *